(12) United States Patent
Patel et al.

(10) Patent No.: US 6,635,807 B1
(45) Date of Patent: Oct. 21, 2003

(54) CANOLA CULTIVAR 44A53

(75) Inventors: Jayantilal D. Patel, Thornhill (CA); Alan W. Grombacher, Beaumont (CA)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 09/795,724

(22) Filed: Feb. 28, 2001

(51) Int. Cl.$^7$ .............................. A01H 5/00; A01H 5/10; A01H 1/02; C12N 5/04

(52) U.S. Cl. ...................... 800/306; 800/303; 800/260; 435/410; 435/421; 435/430

(58) Field of Search ............................... 536/23.1, 23.6, 536/24.3; 435/4, 410, 419, 421, 430; 800/260, 264, 265, 266, 267, 268, 278, 287, 298, 299, 301, 302, 300

(56) References Cited

U.S. PATENT DOCUMENTS 5,523,520 A * 6/1996 Hunsperger et al. ........ 435/410
5,750,871 A * 5/1998 Moloney et al. ......... 435/252.2

OTHER PUBLICATIONS

Bennetzen et al. 1992. Approaches and progress in the molecular cloning of plant disease resistance genes. Genetic Engineering 14:99–124.*

Dion et al. 1995. RFLP mapping of resistance to the blackleg disease [causal agent, Leptospaeria maculans] in canola (Brassica napus L.). Theor. Appl. Genet. 91:1190–1194.*

Eshed et al. 1996. Less–than–additive epistatic interactions of quantitative trait loci in tomato. Genetics 143:1807–1817.*

Goring et al. 1993. An S receptor kinase gene in self–compatible Brassica napus has a 1–bp deletion. The Plant Cell 5:531–539.*

Hemmat et al. 1998. Molecular markers for the scab resistance region in apple. J. Amer. Soc. Hort. Sci. 123(6):992–996.*

Kott et al. 1990. The role of biotechnology in canola/rapeseed research. Pp. 47–78, In: Rapeseed Production, Nutrition, and Technology. Van Reinold, NewYork.*

Kraft et al. 2000. Linkage disequilibrium and fingerprinting in sugar beet. Theor. Appl. Genet. 323–326.*

Michelmore et al. 1991. Identification of markers linked to disease–resistance genes by bulked segregant analysis: a rapid method to detect markers in specific genomic regions by using segregating populations. Proc. Natl. Acad. Sci. (USA):88:9828–9832.* van Ooijen et al. 1994. An RFLP linkage map of Lycopersicon peruvianum. Theor. Appl. Genet. 89:1007–1013.*

Pang et al. 1992. Expression of a gene encoding scorpion insectotoxin peptide in yeast, bacteria, and plants. Gene 116:165–172.*

King et al. 1986. Photoperiod response of spring oilseed rap (Brassica napus L. and B. campestris L.). Field Crops Res. 13:367–373.*

Barsby, T.L., "A Rapid and Efficient Alternative Procedure for the Regeneration of Plants from Hypocotyl Protoplasts of Brassica napus", plant Cell Reports, (1986) (Abstract.

Chuong, Phan V., "a Simple Culture Method for Brassica Hypototyl Protoplasts", Plant Cell Reports, 4:4–6 (1085).

Kartha, K.K., In vitro Plant Formation from Stem Explants of Rape (Brassica napus cv. Zephyr), Physiol. Plant., 31:217–220 (1974).

Narasimhulu S.B., "Species specific shoot regeneration response of cotyledonary explants Brassocas", Plant Cell Reports, 7:104–106 (1988).

Swanson, Eric B., Chapter 17, p. 159, "Microspore Culture in Brassica", Methods in Molecular Biology, vol. 6, Plant Cell and Tissue Culture, Edt. Jeffrey W. Pollard and John M. Walker, by the Humana Press.

* cited by examiner

*Primary Examiner*—Elizabeth F. McElwain
(74) *Attorney, Agent, or Firm*—McKee, Voorhees & Sease, P.L.C.

(57) ABSTRACT

A canola cultivar designated 44A53, plants and seeds of the 44A53 canola cultivar, methods for producing a canola plant produced by crossing the 44A53 cultivar with itself or with another canola plant, and hybrid canola seeds and plants produced by crossing the 44A53 cultivar with another canola line or plant are provided.

20 Claims, No Drawings

CANOLA CULTIVAR 44A53

FIELD OF THE INVENTION

The invention is in the field of *Brassica napus* breeding (i.e., canola breeding), specifically relating to the inbred canola cultivar designated 44A53.

BACKGROUND OF THE INVENTION

The present invention relates to a new and distinctive rapeseed cultivar designated 44A53 which is the result of years of careful breeding and selection. Since such cultivar is of high quality and possesses a relatively low level of erucic acid in the vegetable oil component and a relatively low level of glucosinolate content in the meal component, it can be termed "canola" in accordance with the terminology commonly used by plant scientists.

The creation of new superior, agronomically sound, and stable high yielding cultivars of many plant types including canola has posed an ongoing challenge to plant breeders. In the practical application of a chosen breeding program, the breeder often initially selects and crosses two or more parental lines, followed by repeated selfing and selection, thereby producing many unique genetic combinations. The breeder can theoretically generate billions of different genetic combinations via crossing, selfing and mutagenesis. However, the breeder commonly has no direct control at the cellular level of the plant. Therefore, two breeders will never independently develop the same line, or even very similar lines, having the same canola traits.

Each year, the plant breeder selects the germplasm to advance to the next generation. This germplasm is grown under unique and different geographical, climatic and soil conditions, and further selections are then made during and at the end of the growing season. The characteristics of the cultivars which are developed are incapable of prediction in advance. This unpredictability is because the selection occurs in unique environments, with no control at the DNA level (using conventional breeding procedures), and with millions of different possible genetic combinations being generated. A breeder of ordinary skill cannot predict in advance the final resulting lines that are to be developed, except possibly in a very gross and general fashion. Even the same breeder is incapable of producing the same cultivar twice by using the same original parents and the same selection techniques. This unpredictability commonly results in the expenditure of large research monies and effort to develop a new and superior canola cultivar.

It is recognized that mass and recurrent selections can be used to improve populations of either self-or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line that is the recurrent parent. The source of the trait to be transferred is called the donor parent. The resulting plant is expected to have the attributes of the recurrent parent (e.g. cultivar) and the desirable trait transferred from the donor parent. After the initial cross, individuals possessing the phenotype of the donor parent are selected and are repeatedly crossed (backcrossed) to the recurrent parent. The resulting plant is expected to have the attributes of the recurrent parent (e.g., cultivar) and the desirable trait transferred from the donor parent. This approach has been used extensively for breeding disease resistant cultivars of many plant types.

Each breeding program should include a periodic, objective evaluation of the efficiency of the breeding procedure. Evaluation criteria varies depending on the goal and objectives, but should include gain from selection per year based on comparisons to an appropriate standard, the overall value of the advanced breeding lines, and the number of successful cultivars produced per unit of input (e.g., per year, per dollar expended, etc.).

Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Promising advanced breeding lines commonly are thoroughly tested and are compared to appropriate standards in environments representative of the commercial target area(s) for three or more years. The best lines are candidates for new commercial cultivars; and those still deficient in a few traits may be used as parents to produce new populations for further selection.

These processes, which lead to the final step of marketing and distribution, usually take from approximately eight to twelve years from the time the first cross is made. Therefore, the development of new cultivars such as that of the present invention is a time-consuming process that requires precise forward planning, efficient use of resources, and a minimum of changes in direction.

A most difficult task is the identification of individuals that are genetically superior, because for most traits the true genotypic value may be masked by other confounding plant traits or environmental factors. One method for identifying a superior plant is to observe its performance relative to other experimental plants and to one or more widely grown standard cultivars. If a single observation is inconclusive, replicated observations provide a better estimate of the genetic worth.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

The choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences the choice of the breeding method. Pedigree breeding and recurrent selection breeding methods are used to develop cultivars from breeding populations. Pedigree breeding starts with the crossing of two genotypes, each of which may have one or more desirable characteristics that is lacking in the other or which complements the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \to F_2$; $F_2 \to F_3$; $F_3 \to F_4$; $F_4 \to F_5$, etc.

Pedigree breeding is commonly used for the improvement of largely self-pollinating crops such as canola. Two parents that are believed to possess favorable, complementary traits are crossed to produce an $F_1$. An $F_2$ population is produced by selfing one or several $F_1$'s or by intercrossing two $F_1$'s (i.e., sib mating). Selection of the best individuals may begin in the $F_2$ population, and beginning in the $F_3$ the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines commonly are tested for potential release as new cultivars.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, canola breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

If desired the haploidy method can be used to extract homogeneous lines.

Proper testing should detect any major faults and establish the level of superiority or improvement over current cultivars. In addition to showing superior performance, there must be a demand for a new cultivar that is compatible with industry standards or which creates a new market. The introduction of a new cultivar commonly will incur additional costs to the seed producer, the grower, the processor and the consumer, for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Currently *Brassica napus* canola is being recognized as an increasingly important oilseed crop and a source of meal in many parts of the world. The oil as removed from the seeds commonly contains a lesser concentration of endogenously formed saturated fatty acids than other vegetable oils and is well suited for use in the production of salad oil or other food products or in cooking or frying applications. The oil also finds utility in industrial applications. Additionally, the meal component of the seeds can be used as a nutritious protein concentrate for livestock.

*Brassica napus* canola plants are recognized to commonly be self-fertile with approximately 70 to 90 percent of the seed normally forming as the result of self-pollination. The percentage of cross pollination may be further enhanced when populations of recognized insect pollinators at a given growing site are greater.

SUMMARY OF THE INVENTION

According to the present invention, there is provided a novel *Brassica napus* cultivar designated 44A53. This invention thus relates to the seeds of the 44A53 cultivar, to plants of the 44A53 cultivar, and to methods for producing a canola plant produced by crossing the 44A53 cultivar with itself or another canola line.

DEFINITIONS

In the description and tables which follow a number of terms are used. In order to aid in a clear and consistent understanding of the specification the following definitions and evaluation criteria are provided.

Type. This refers to whether the new cultivar is considered to be primarily a Spring or Winter type of canola.

Ploidy. This refers to whether the number of chromosomes exhibited by the cultivar is diploid or tetraploid.

Cotyledon. A cotyledon is a type of seed leaf; a small leaf contained on a plant embryo. A cotyledon contains the food storage tissues of the seed. The embryo is a small plant contained within a mature seed.

Cotyledon Length. The distance between the indentation at the top of the cotyledon and the point where the width of the petiole is approximately 4 mm.

Cotyledon Width. The width at the widest point of the cotyledon when the plant is at the two to three-leaf stage of development (mean of 50).

Leaf Color. The leaf blade coloration is observed when at least 6 leaves of the plant are completely developed.

Leaf Attachment to Stem. The presence or absence of clasping where the leaf attaches the stem, and when present the degree thereof are observed.

Leaf Glaucousity. The presence or absence of a fine whitish powdery coating on the surface of the leaves, and the degree thereof when present are observed.

Leaf Lobes. The fully developed upper stem leaves are observed for the presence or absence of leaf lobes when at least 6 leaves of the plant are completely developed.

Number of Leaf Lobes. The frequency of leaf lobes when present is observed when at least 6 leaves of the plant are completely developed.

Leaf Surface. The leaf surface is observed for the presence or absence of wrinkles when at least 6 leaves of the plant are completely developed.

Leaf Dentation. The margins of the upper stem leaves are observed for the presence or absence of indentation or serration, and the degree thereof if present when at least 6 leaves of the plant are completely developed.

Leaf Length. The length of the leaf blades and petioles are observed when at least 6, leaves of the plant are completely developed (mean of 50).

Leaf Width. The width of the leaf blades are observed when at least 6 leaves of the plant are completely developed (mean of 50).

Leaf Margin Hairiness. The leaf margins of the first leaf are observed for the presence or absence of pubescence, and the degree thereof when the plant is at the two leaf-stage.

Leaf Upper Side Hairiness. The upper surfaces of the leaves are observed for the presence or absence of hairiness, and the degree thereof if present when at least 6 of the leaves of the plant are formed.

Leaf Attitude. The disposition of typical leaves with respect to the petiole is observed when at least 6 leaves of the plant are formed.

Leaf Tip Reflexion. The presence or absence of bending of typical leaf tips and the degree thereof, if present are observed at the 6 to 11 leaf-stage.

Leaf Anthocyanin Coloration. The presence or absence of leaf anthocyanin coloration and the degree thereof if present are observed when the plant has reached the 9 to 11 leaf-stage.

Petiole Length. The length of the petioles is observed in a cultivar forming lobed leaves when at least 6 leaves of the plant are completely developed.

Stem Anthocyanin Coloration. The presence or absence of leaf anthocyanin coloration and the intensity thereof if present are observed when the plant has reached the 9 to 11 leaf-stage.

Speed of Root Formation. The typical speed of root formation is observed when the plant has reached the 4 to 11 leaf-stage.

Root Depth in Soil. The typical root depth is observed when the plant has reached at least the 6 leaf-stage.

Root Chlorophyll Coloration. The presence or absence of chlorophyll coloration in the skin at the top of the root is observed when the plant has reached at least the 6 leaf-stage.

Root Anthocyanin Coloration. The presence or absence of anthocyanin coloration in the skin at the top of the root is observed when the plant has reached at least the 6 leaf-stage.

Root Anthocyanin Expression. When anthocyanin coloration is present in skin at the top of the root, it further is observed for the exhibition of a reddish or bluish cast within such coloration when the plant has reached at least the 6 leaf-stage.

Root Anthocyanin Streaking. When anthocyanin coloration is present in the skin at the top of the root, it further is observed for the presence or absence of streaking within such coloration when the plant has reached at least the 6 leaf-stage.

Root Coloration Below Ground. The coloration of the root skin below ground is observed when the plant has reached at least the 6 leaf-stage.

Root Flesh Coloration. The internal coloration of the root flesh is observed when the plant has reached at least the 6 leaf-stage.

Seedling Growth Habit. The growth habit of young seedlings is observed for the presence of a weak (1) or strong (9) rosette character and is expressed on a scale of 1 to 9.

Plant Height. The overall plant height at the end of flowering is observed (mean of 50).

Time of Flowering. A determination is made of the number of days when at least 50 percent of the plants have one or more open buds on a terminal raceme in the year of sowing.

Flower Bud Location. A determination is made whether typical buds are disposed above or below the most recently opened flowers.

Flower Petal Coloration. The coloration of open exposed petals on the first day of flowering is observed.

Petal Length. The lengths of typical petals of fully opened flowers are observed (mean of 50).

Petal Width. The widths of typical petals of fully opened flowers are observed (mean of 50).

Anther Dotting. The level of anther dotting when the flowers are fully opened is observed.

Anther Arrangement. The general disposition of the anthers in typical fully opened flowers is observed.

Pollen Formation. The relative level of pollen formation is observed at the time of dehiscence.

Pod Type. The overall configuration of the silique is observed.

Pod Length. The typical silique length is observed and is expressed on a scale of 1 (short) to 5 (long).

Pod Width. The typical silique width when mature is observed and is expressed on a scale of 1 (narrow) to 5 (wide).

Pedicel Length. The typical length of the silique peduncle when mature is observed and is expressed on a scale of 1 (short) to 5 (long).

Length of Beak. The typical length of the silique beak when mature is observed and is expressed on a scale of 1 (short) to 5 (long).

Pod Anthocyanin Coloration. The presence or absence at maturity of silique anthocyanin coloration, and the degree thereof if present are observed.

Pod Habit. The typical manner in which the silique are borne on the plant at maturity is observed.

Maturity. The number of days from planting to maturity is observed with maturity being defined as the plant stage when pods with seed color change, occuring from green to brown or black, on the bottom third of the pod bearing area of the main stem.

Seeds Per Pod. The average number of seeds per pod is observed (mean of 50).

Seed Size. The weight in grams of 1,000 typical seeds is determined at maturity while such seeds exhibit a moisture content of approximately 5 to 6 percent by weight.

Seed Coat Color. The seed coat color of typical mature seeds is observed.

Seed Coat Mucilage. The presence or absence of mucilage on the seed coat is determined and is expressed on a scale of 1 (absent) to 9 (heavy). During such determination a petri dish is filled to a depth of 0.3 cm. with tap water provided at room temperature. Seeds are added to the petri dish and are immersed in water where they are allowed to stand for five minutes. The contents of the petri dish containing the immersed seeds next is examined under a stereo microscope equipped with transmitted light. The presence of mucilage and the level thereof is observed as the intensity of a halo surrounding each seed.

Oil Content: The typical percentage by weight oil present in the mature whole dried seeds is determined by ISO 10565:1993 Oilseeds Simultaneous determination of oil and water—Pulsed NMR method. Also, oil could be analyzed using NIR (Near Infra Red sprectoscopy) as long as the instrument is calibrated and certified by Grain Research Laboratory of Canada.

Protein Content: The typical percentage by weight of protein in the oil free meal of the mature whole dried seeds is determined by AOCS Official Method Ba 4e-93 Combustion Method for the Determination of Crude Protein. Also, protein could be analyzed using NIR (Near Infra Red sprectoscopy) as long as the instrument is calibrated and certified by Grain Research Laboratory of Canada.

Fatty Acid Content: The typical percentages by weight of fatty acids present in the endogenously formed oil of the mature whole dried seeds are determined. During such determination the seeds are crushed and are extracted as fatty acid methyl esters following reaction with methanol and sodium methoxide. Next the resulting ester is analyzed for fatty acid content by gas liquid chromatography using a capillary column which allows separation on the basis of the degree of unsaturation and fatty acid chain length. This procedure is described in the work of J. K. Daun et al. *J. Amer. Oil Chem. Soc.*, 60: 1751 to 1754 (1983) which is herein incorporated by reference.

Chlorophyll Content. The typical chlorophyll content of the mature seeds is determined by using methods recommended by the WCC/RRC and is considered to be low if <8 ppm, medium if 8 to 15 ppm, and high if 15 to 30 ppm.

Glucosinolate Content. The total glucosinolates of seed at 8.5% moisture as measured by AOCS Official Method AK-1-92 (Determination of glucosinolates content in rapeseed-colza by HPLC) is expressed micromoles per gram. Capillary gas chromatography of the trimethylsityl derivatives of extracted and purified desulfoglucosinolates with optimization to obtain optimum indole glucosinolate detection as described in *"Procedures of the Western Canada Canola/Rapeseed Recommending Committee Incorporated for the Evaluation and Recommendation for Registration of Canola/Rapeseed Candidate Cultivars in Western Canada"*.

TGF Resistance to Shattering. Resistance to silique shattering is observed at seed maturity and is expressed on a scale of 1 (poor) to 5 (excellent).

Resistant to Lodging. Resistance to lodging at the maturity and is expressed on a scale of 1 (weak) to 5 (strong).

Frost Tolerance (Spring Type Only). The ability of young plants to withstand late spring frosts at a typical growing area is evaluated and is expressed on a scale of 1 (poor) to 5 (excellent).

Winter Survival (Winter Type Only). The ability to withstand winter temperatures at a typical growing area is evaluated and is expressed on a scale of 1 (poor) to 5 (excellent).

Disease Resistance: Resistant to various diseases is evaluated and is expressed on a scale of 0 highly resistant, 5=highly susceptible. The WCC/RRC blackleg classification is based on % severity index described as follows:

0–30%=Resistant
30%–50%=Moderately Resistant
50%–70%=Moderately Susceptible
70%–90%=Susceptible
\>90%=Highly susceptible.

The % severity index=blackleg rating on 0–5 for a variety/blackleg rating for HS variety Westar.

Herbicide Resistance: Resistance to various herbicides when applied at standard recommended application rates is expressed on a scale of 1 (resistant), 2 (tolerant), or 3 (susceptible).

DETAILED DESCRIPTION OF THE INVENTION

A canola cultivar needs to be homogeneous, homozygous and reproducible to be useful for the production of a commercial crop on a reliable basis. There are a number of analytical methods available to determine the homozygotic and phenotypic stability of a canola cultivar.

The oldest and most traditional method of analysis is the observation of phenotypic traits. The data is usually collected in field experiments over the life of the canola plants to be examined. Phenotypic characteristics most often are observed for traits associated with seed yield, seed oil content, seed protein content, fatty acid composition of oil, glucosinolate content of meal, growth habit, lodging resistance, plant height, shattering resistance, etc.

In addition to phenotypic observations, the genotype of a plant can also be examined. There are many laboratory-based techniques available for the analysis, comparison and characterization of plant genotype; among these are isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

The cultivar of the present invention has shown uniformity and stability for all traits, as described in the following cultivar description information. It has been self-pollinated a sufficient number of generations, with careful attention to uniformity of plant type to ensure homozygosity and phenotypic stability. The cultivar has been increased with continued observation for uniformity. The frequency of variants in this variety is less than 1/10,000.

Cultivar 44A53 demonstrates a substantial degree of glyphosate resistance. It is an early variety and demonstrates above average yield. 44A53 also exhibits resistance to blackleg disease and is specially adapted for and performs consistently in the mid and short season canola growing areas of Western Canada.

Morphological

Since canola cultivar 44A53 is substantially homogeneous, it can be reproduced by planting seeds of such cultivar, growing the resulting canola plants under self-pollinating or sib-pollinating conditions with adequate isolation, and harvesting the resulting seed using conventional agronomic practices.

TABLE 1

VARIETY DESCRIPTION INFORMATION
44A53

| | |
|---|---|
| 1. | Species: *Brassica napus* |
| 2. | Type: Spring |
| 3. | Plant Height: |
| | 103.2 cm Tall |
| | 21.0 cm shorter than Defender |
| | Height Class: (Spring sown) medium short |
| 4. | Stem Anthocyanin: weak |
| 5. | Seed Cotyledons: medium (Primor) |
| 6. | Seedling Growth Habit (leaf rosette): upright to prostrate |
| 7. | Leaves: |
| | Margins: medium (Primor) |
| | Lobing: medium (Primor) |
| | Leaf Attachment to stem: partial clasping |
| | Color: medium dark green |
| | Glaucosity: weak to medium to medium |

TABLE 1-continued

VARIETY DESCRIPTION INFORMATION 44A53

8. Flowers:

Flower Buds Location: Buds at tip of apical meristem
   Petal color: yellow
   Flowering class: (Spring sown) early 9. Pods:

Pod type: bilateral single pod
   Silique beak length: long
   Pod length: medium
   Pod width: wide
   Pod habit: semi-erect
   Pedicel length: short to long
   Ripening class: medium
   Days to maturity: 95.0

10. Seeds:

Unsized seed: 3.44 g/1000
    0.19 g more than Defender
    Weight class: 3.0–3.9 g
    Seeds per pod: N/A
    Testa color: back 11. Chemical composition of seed:

Erucic acid: low
    Glucosinate content: (based on 11.1 millimoles/g): low
    % Oil: 48.4
    Protein: 47.4
    Fatty acid composition:

Palmitic: 3.91
    Stearic: 1.92
    Oleic: 64.31
    Linoleic: 19.21
    Linolenic: 8.29
    Eicosenoic: 1.17
    Erucic: 0.00

12. Frost tolerance: Moderately susceptible
13. Lodging resistance: moderately strong
14. Herbicide resistance:

Atrazine: susceptible
    Glyphosate: resistant

15. Disease resistance:

Sclerotinia Stem Rot: susceptible
    Black Leg, Stem Canker: high resistance
    White Rust: high resistance
    Light Leaf Spot: not tested
    Downy Mildew: not tested
    Rhizoctonia Root Rot: not tested
    Alternaria Black Spot: not tested When preparing the detailed phenotypic information that follows, plants of the new 44A53 cultivar were observed while growing using conventional agronomic practices. For comparative purposes canola plants of four publicly available canola cultivars were similarly grown in isolation at the same location and were observed under the same growing conditions. The results are shown in table 2.

From review of the table, cultivar 44A53 exhibits a unique blade color, depth or margin dent, and leaf length which is not seen in any of the comparison varieties. Cultivar 44A53 clearly possesses a unique combination of morphological traits.

TABLE 2

| MORPHOLOGICAL TRAIT | 44A53 | DEFENDER | EXCEL | LEGACY | 45A51 |
| --- | --- | --- | --- | --- | --- |
| Canola Type | Spring | Spring | Spring | Spring | Spring |
| Cotyledon Width | medium | medium | medium | medium | medium to wide |
| cotyledon tength | medium | medium | medium | medium | medium to long |
| blade color | medium to dark green | dark green | dark green | dark green | dark green |
| number of lobes | medium | medium | few to medium | medium | few to medium |
| leaf depth of margin dent | medium | deep | shallow | deep | shallow |
| leaf length | short to medium | medium | medium | long | medium |
| leaf width | medium to wide | medium to wide | medium | wide | medium |
| petiole length | medium | medium to long | medium to long | medium | medium |
| petal color | yellow | yellow | yellow | yellow | yellow |
| petal length | medium | medium | medium | medium | medium |
| petal width | medium | medium | medium | wide | medium |
| anther fertility | shedding pollen | shedding pollen | shedding pollen | shedding pollen | shedding pollen |
| siligue attitude | semi-erect | horizontal | horizontal | horizontal | semi-erect |
| siligue length | medium | long | medium to long | medium | medium |
| siligue width | wide | medium | narrow | medium | narrow |
| beak length | long to v. long | long | long to v.long | long | medium |
| pedicte length | medium | long | medium | long | medium |
| seed coat color | black | black | black | black | black |

FURTHER EMBODIMENTS OF THE INVENTION

Transformation of Canola

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign, additional and/or modified genes are referred to herein collectively as "transgenes". Over the last fifteen to twenty years several methods for producing transgenic plants have been developed, and the present invention, in particular embodiments, also relates to transformed versions of the claimed variety or line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed canola plants, using transformation methods as described below to incorporate transgenes into the genetic material of the canola plant(s).

Hf Expression Vectors for Canola Transformation

Marker Genes

Expression vectors may include a genetic marker, operably linked to a regulatory element (a promoter, for example) that allows transformed cells containing the marker to be either recovered by negative selection, i.e. inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

Marker genes can include, but are not limited to, the following:

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Natl. Acad. Sci. U.S.A.*, 80: 4803 (1983). Another commonly used selectable marker gene is the hygromycin phosphotransferase gene which confers resistance to the antibiotic hygromycin. Vanden Elzen et al., *Plant Mol. Biol.*, 5: 299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86: 1216 (1988), Jones et al., *Mol. Gen. Genet.*, 210: 86 (1987), Svab et al., *Plant Mol. Biol.* 14: 197 (1990), Hille et al., *Plant Mol. Biol.* 7.: 171 (1986). Other selectable marker genes confer resistance to herbicides such as glyphosate, glufosinate or broxynil. Comai et al., *Nature* 317: 741–744 (1985), Gordon-Kamm et al., *Plant Cell* 2: 603–618 (1990) and Stalker et al., *Science* 242: 419–423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13: 67 (1987), Shah et al., *Science* 233: 478 (1986), Charest et al., Plant Cell Rep. 8: 643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include-glucuronidase (GUS), β-galactosidase, luciferase and chloramphenicol acetyltransferase. Jefferson, R. A., *Plant Mol. Biol. Rep.* 5: 387 (1987)., Teeri et al., *EMBO J.* 8: 343 (1989), Koncz et al., *Proc. Natl. Acad. Sci. U.S.A.* 84:131 (1987), De Block et al., EMBO J. 3: 1681 (1984).

Recently, in vivo methods for visualizing luciferase activity that do not require destruction of plant tissue have been made available. Molecular Probes Publication 2908, Imagene Green™, p. 1–4 (1993) and Naleway et al., *J. Cell Biol.* 115: 151a (1991). However, these in vivo methods for visualizing luciferase activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263: 802 (1994). GFP and mutants of GFP may be used as screenable markers.

Marker genes can be linked to the gene of interest, or can be segregated away or excised in the final product (Yoder and Goldsborough Bio/technology, Vol. 12, March 1994).

Promoters

Genes included in expression vectors must be driven by a nucleotide sequence comprising a regulatory element, for example, a promoter. Several types of promoters are now well known in the transformation arts, as are other regulatory elements that can be used alone or in combination with promoters. As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in canola. Optionally, the inducible promoter is operably linked to a nucleotide sequence encoding a signal sequence which is operably linked to a gene for expression in canola. With an inducible promoter the rate of transcription increases in response to an inducing agent.

Any inducible promoter can be used in the instant invention. See Ward et al. *Plant Mol. Biol.* 22: 361–366 (1993). Exemplary inducible promoters include, but are not limited to, that from the ACEI system which responds to copper (Mett et al. *PNAS* 90: 4567–4571 (1993)); In2 gene from maize which responds to benzenesulfonamide herbicide safeners (Hershey et al., *Mol. Gen. Genetics* 227: 229–237 (1991) and Gatz et al., *Mol. Gen. Genetics* 243: 32–38 (1994)) or Tet repressor from Tn10 (Gatz et al., *Mol. Gen. Genet.* 227: 229–237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88: 0421 (1991).

B. Constitutive Promoters

A constitutive promoter is operably linked to a gene for expression in canola or the constitutive promoter is operably linked to a nucleotide sequence encoding a signal sequence which is operably linked to a gene for expression in canola.

Many different constitutive promoters can be utilized in the instant invention. Exemplary constitutive promoters include, but are not limited to, the promoters from plant viruses such as the 35S promoter from CaMV (Odell et al., *Nature* 313: 810–812 (1985) and the promoters from such genes as rice actin (McElroy et al., *Plant Cell* 2: 163–171 (1990)); ubiquitin (Christensen et al., *Plant Mol. Biol.* 12: 619–632 (1989) and Christensen et al., *Plant Mol. Biol.* 18: 675–689 (1992)); pEMU (Last et al., *Theor. Appl. Genet.* 81: 581–588 (1991)); MAS (Velten et al., *EMBO J.* 3: 2723–2730 (1984)) and maize H3 histone (Lepetit et al., *Mol. Gen. Genet.* 231: 276–285 (1992) and Atanassova et al., *Plant Journal* 2 (3): 291–300 (1992)).

The ALS promoter, a XbaI/NcoI fragment 5' to the *Brassica napus* ALS3 structural gene (or a nucleotide sequence that has substantial sequence similarity to said XbaI/NcoI fragment), represents a particularly useful constitutive promoter. See PCT application WO96/30530. In addition, constitutive promoters may be chimaric and synthetic, for example SCP1 (U.S. patent application Ser. No. 09/028,819 (Case No. 0452RJ).

C. Tissue-specific or Tissue-preferred Promoters

A tissue-specific promoter is operably linked to a gene for expression in canola. Optionally, the tissue-specific promoter is operably linked to a nucleotide sequence encoding a signal sequence which is operably linked to a gene for expression in canola. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter—such as that from the phaseolin gene (Murai et al., *Science* 23: 476–482 (1983) and Sengupta-Gopalan et al., *Proc. Natl. Acad. Sci. USA* 82: 3320–3324 (1985)); a leaf-specific and light-induced promoter such as that from cab or rubisco (Simpson et al., *EMBO J.* 4(11): 2723–2729 (1985) and Timko et al., *Nature* 318: 579–582 (1985)); an anther-specific promoter such as that from LAT52 (Twell et al., *Mol. Gen. Genet.* 217: 240–245 (1989)); a pollen-specific promoter such as that from Zm13 (Guerrero et al., *Mol. Gen. Genet.* 224: 161–168 (1993); a microspore-preferred promoter such as that from apg (Twell et al., *Sex. Plant Reprod.* 6: 217–224 (1993); and anther specific promoters such as Bp4, Bp10, Bp19 and Bnm1 (Fabijanski et al., In Vitro Cell Dev. Biol. 28:46–52 (1992) and Treacy et al., Pi. Mol. Biol. 34:603–611 (1997).

Signal Sequences for Targeting Proteins to Subcellular Compartments

Transport of protein produced by transgenes to a subcellular compartment such as the chloroplast, vacuole, peroxisome, glyoxysome, cell wall or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., *Plant Mol. Biol.* 20: 49 (1992), Close, P. S., Master's Thesis, Iowa State University (1993), Knox, C., et al., "Structure and Organization of Two Divergent Alpha-Amylase Genes From Barley", *Plant Mol. Biol.* 9: 3–17 (1987), Lerner et al., *Plant Physiol.* 91: 124–129 (1989), Fontes et al., *Plant Cell* 3: 483–496 (1991), Matsuoka et al., *Proc. Natl. Acad. Sci.* 88: 834 (1991), Gould et al., *J. Cell Biol* 108: 1657 (1989), Creissen et al., *Plant J.* 2: 129 (1991), Kalderon, D., Robers, B., Richardson, W., and Smith A., "A short amino acid sequence able to specify nuclear location", *Cell* 39: 499–509 (1984), Stiefel, V., Ruiz-Avila, L., Raz R., Valles M., Gomez J., Pages M., Martinez-Izquierdo J., Ludevid M., Landale J., Nelson T., and Puigdomenech P., "Expression of a maize cell wall hydroxyproline-rich glycoprotein gene in early leaf and root vascular differentiation", *Plant Cell* 2: 785–793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114: 92–6 (1981).

According to a preferred embodiment, the transgenic plant provided for commercial production of foreign protein is a canola plant. In another preferred embodiment, the biomass of interest is seed.

For the relatively small number of transgenic plants that show high levels of expression, a genetic map can be generated, primarily via conventional RFLP, PCR, and SSR analysis, which identifies the approximate chromosomal location of the integrated DNA molecule. For exemplary methodologies in this regard, see Glick and Thompson, Methods in Plant Molecular Biology and Biotechnology 269–284 (CRC Press, Boca Raton, 1993). Map information concerning chromosomal location is useful for proprietary protection of a subject transgenic plant. If unauthorized propagation is gundertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below.

1. Genes That Confer Resistance To Pests or Disease And That Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., *Science* 266: 789 (1994) (cloning of the tomato Cf-9 gene for resistance to *Cladosporium fulvum*); Martin et al., *Science* 262: 1432 (1993) (tomato Pto gene for resistance to *Pseudomonas syringae pv.* tomato encodes a protein kinase); Mindrinos et al., *Cell* 78: 1089 (1994) (Arabidopsis RSP2 gene for resistance to *Pseudomonas syringae*).

(B) A gene conferring resistance to fungal pathogens, such as oxalate oxidase or oxalate decarboxylase (Zhou et al., *Pl. Physiol.* 117(1):33–41 (1998)).

(C) A *Bacillus thuringiensis* protein, a derivative thereof or a synthetic polypeptide modeled thereon. See, for example, Geiser et al., *Gene* 48: 109 (1986), who disclose the cloning and nucleotide sequence of a Bt δ-endotoxin gene. Moreover, DNA molecules encoding δ-endotoxin genes can be purchased from American Type Culture Collection (Manassas, Va.), for example, under ATCC Accession Nos. 40098, 67136, 31995 and 31998.

(D) A lectin. See, for example, the disclosure by Van Damme et al., *Plant Molec. Biol.* 24: 25 (1994), who disclose the nucleotide sequences of several *Clivia miniata* mannose-binding lectin genes.

(E) A vitamin-binding protein such as avidin. See PCT application U.S. Ser. No. 93/06487, the contents of which are hereby incorporated by reference. The application teaches the use of avidin and avidin homologues as larvicides against insect pests.

(F) An enzyme inhibitor, for example, a protease or proteinase inhibitor or an amylase inhibitor. See, for example, Abe et al., *J. Biol. Chem.* 262: 16793 (1987) (nucleotide sequence of rice cysteine proteinase inhibitor), Huub et al., *Plant Molec. Biol.* 21: 985 (1993) (nucleotide sequence of cDNA encoding tobacco proteinase inhibitor 1), Sumitani et al., *Biosci. Biotech. Biochem.* 57: 1243 (1993) (nucleotide sequence of Streptomyces nitrosporeus α-amylase inhibitor) and U.S. Pat. No. 5,494,813 (Hepher and Atkinson, issued Feb. 27, 1996).

(G) An insect-specific hormone or pheromone such as an ecdysteroid and juvenile hormone, a variant thereof, a mimetic based thereon, or an antagonist or agonist thereof. See, for example, the disclosure by Hammock et al., *Nature* 344: 458 (1990), of baculovirus expression of cloned juvenile hormone esterase, an inactivator of juvenile hormone.

(H) An insect-specific peptide or neuropeptide which, upon expression, disrupts the physiology of the affected pest. For example, see the disclosures of Regan, *J. Biol. Chem.* 269: 9 (1994) (expression cloning yields DNA coding for insect diuretic hormone receptor), and Pratt et al., *Biochem. Biophys. Res. Comm.* 163: 1243 (1989) (an allostatin is identified in *Diploptera puntata*). See also U.S. Pat. No. 5,266,317 to Tomalski et al., who disclose genes encoding insect-specific, paralytic neurotoxins.

(I) An insect-specific venom produced in nature by a snake, a wasp, etc. For example, see Pang et al., *Gene* 116: 165 (1992), for disclosure of heterologous expression in plants of a gene coding for a scorpion insectotoxic peptide.

(J) An enzyme responsible for an hyperaccumulation of a monterpene, a sesquiterpene, a steroid, hydroxamic acid, a phenylpropanoid derivative or another non-protein molecule with insecticidal activity.

(K) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23: 691 (1993), who teach the nucleotide sequence of a cDNA encoding tobacco hookworm chitinase, and Kawalleck et al., *Plant Molec. Biol.* 21: 673 (1993), who provide the nucleotide sequence of the parsley ubi4-2 polyubiquitin gene.

(L) A molecule that stimulates signal transduction. For example, see the disclosure by Botella et al., *Plant Molec. Biol.* 24: 757 (1994), of nucleotide sequences for mung bean calmodulin cDNA clones, and Griess et al., *Plant Physiol.* 104: 1467 (1994), who provide the nucleotide sequence of a maize calmodulin cDNA clone.

(M) A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

(N) A membrane permease, a channel former or a channel blocker. For example, see the disclosure by Jaynes et al., *Plant Sci.* 89: 43 (1993), of heterologous expression of a cecropin-β lytic peptide analog to render transgenic tobacco plants resistant to *Pseudomonas solanacearum*.

(O) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(P) An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molercular Plant-microbe Ineractions (Edinburgh, Scotland, 1994) (enzymatic inactivation in transgenic tobacco via production of single-chain antibody fragments).

(Q) A virus-specific antibody. See, for example, Tavladoraki et al., *Nature* 366: 469 (1993), who show that transgenic plants expressing recombinant antibody genes are protected from virus attack.

(R) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., *Bio/Technology* 10: 1436 (1992). The cloning and characterization of a gene which encodes a bean endopolygalacturonase-inhibiting protein is described by Toubart et al., *Plant J.* 2: 367 (1992).

(S) A developmental-arrestive protein produced in nature by a plant. For example, Logemann et al., *Bio/Technology* 10: 305 (1992), have shown that transgenic plants expressing the barley ribosome-ina encoding a mutant aroA gene can be obtained under ATCC accession No. 39256, and the nucleotide sequence of the mutant gene is disclosed in U.S. Pat. No. 4,769,061 to Comai. European patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al. De Greef et al., *Bio/Technology* 7: 61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop, are the Accl-S1, Accl-S2 and Accl-S3 genes described by Marshall et al., *Theor. Appl. Genet.* 83: 435 (1992).

(C) A herbicide that inhibits photosynthesis, such as a triazine (psbA and gs+ genes) and a benzonitrile (nitrilase gene). Przibilla et al., *Plant Cell* 3: 169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., *Biochem. J.* 285: 173 (1992).

3. Genes That Confer Or Contribute to a Value-Added Trait, Such As:

(A) Modified fatty acid metabolism, for example, by transforming a plant with an antisense gene of stearoyl-ACP desaturase to increase stearic acid content of the plant. See Knultzon et al., *Proc. Nat-'l. Acad. Sci. USA* 89: 2624 (1992).

(B) Decreased Phytate Content
(1) Introduction of a phytase-encoding gene would enhance breakdown of phytate, adding more free phosphate to the transformed plant. For example, see Van Hartingsveldt et al., *Gene* 127: 87 (1993), for a disclosure of the nucleotide sequence of an *Aspergillus niger* phytase gene.
(2) A gene could be introduced that reduces phytate content. In maize, this, for example, could be accomplished, by cloning and then reintroducing DNA associated with the single allele which is responsible for maize mutants characterized by low levels of phytic acid. See Raboy et al., *Maydica* 35: 383 (1 990).

(C) Modified carbohydrate composition effected, for example, by transforming plants with a gene coding for an enzyme that alters the branching pattern of starch. See Shiroza et al., *J. Bacteriol.* 170: 810 (1988) (nucleotide sequence of Streptococcus mutans fructosyltransferase gene), Steinmetz et al., *Mol. Gen. Genet.* 200: 220 (1985) (nucleotide sequence of *Bacillus subtilis* levansucrase gene), Pen et al., *Bio/Technology* 10: 292 (1992) (production of transgenic plants that express *Bacillus licheniformis* α-amylase), Elliot et al., *Plant Molec. Biol.* 21: 515 (1993) (nucleotide sequences of tomato invertase genes), Søgaard et al., *J. Biol. Chem.* 268: 22480 (1993) (site-directed mutagenesis of barley α-amylase gene), and Fisher et al., *Plant Physiol.* 102: 1045 (1993) (maize endosperm starch branching enzyme II).

(D) Reduced green seed, by down regulation of the CAB gene in Canola seed (Abstract #1566, Am. Soc. Pi. Physiol. Meeting 1997, Morisette et al.

4. Genes That Control Pollination or Hybrid Seed Production:

(Canadian Patent Application 2,021,703, PHI Ref. 217-CA and PCT/CA98/00089, PHI Ref. 618P-PCT-CA.

Methods for Canola Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89–119.

The following are examples, and are not limited to:

A. Agrobacterium-mediated Transformation

One method for introducing an expression vector into plants is based on the natural transformation system of Agrobacterium. See, for example, Horsch et al., *Science* 227: 1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10: 1 (1991). Descriptions of Agrobacterum vector systems and methods for Agrobacterium-mediated gene transfer are provided by Gruber et al., supra, Miki et al, supra, and Moloney et al., *Plant Cell Reports* 8: 238 (1989). Bechtold et al., C. R. Acad. Sci. Paris Life Sciences, 316:1194–9 (1993).

B. Direct Gene Transfer

Several methods of plant transformation, collectively referred to as direct gene transfer, have been developed as an alternative to Agrobacterium-mediated transformation. A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5: 27 (1987), Sanford, J. C., *Trends Biotech.* 6: 299 (1988), Klein et al., *Bio/Technology* 6: 559–563 (1988), Sanford, J. C., *Physiol Plant* 79: 206 (1990), Klein et al., *Biotechnology* 10: 268 (1992). See also U.S. Pat. No. 5,015,580 (Christou, et al), issued May 14, 1991; U.S. Pat. No. 5,322,783 (Tomes, et al.), issued Jun. 21, 1994.

Another method for physical delivery of DNA to plants is sonication of target cells. Zhang et al., *Bio/Technology* 9: 996 (1991). Alternatively, liposome or spheroplast fusion have been used to introduce expression vectors into plants.

Deshayes et al., *EMBO J*., 4: 2731 (1985), Christou et al., *Proc Natl. Acad. Sci. U.S.A*. 84: 3962 (1987). Direct uptake of DNA into protoplasts using CaCl2 precipitation, polyvinyl alcohol or poly-L-ornithine have also been reported. Hain et al., *Mol. Gen. Genet*. 199: 161 (1985) and Draper et al, *Plant Cell Physiol*. 23: 451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4: 1495–1505 (1992) and Spencer et al., *Plant Mol. Biol*. 24: 51–61 (1994).

Following transformation of canola target tissues, expression of the above-described selectable marker genes allows for preferential selection of transformed cells, tissues and/or plants, using regeneration and selection methods now well known in the art.

The foregoing methods for transformation would typically be used for producing a transgenic variety. The transgenic variety could then be crossed, with another (non-transformed or transformed) variety, in order to produce a new transgenic variety. Alternatively, a genetic trait which has been engineered into a particular canola line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Tissue Culture of Canola

Further production of the 44A53 cultivar can occur by self-pollination or by tissue culture and regeneration. Tissue culture of various tissues of canola and regeneration of plants therefrom is known. For example, the propagation of a canola cultivar by tissue culture is described in any of the following but not limited to any of the following which are hereby incorporated in their entirety by reference: Chuong et al., "A Simple Culture Method for Brassica hypocotyl Protoplasts", *Plant Cell Reports* 4:4–6 (1985); Barsby, T. L., et al., "A Rapid and Efficient Alternative Procedure for the Regeneration of Plants from Hypocotyl Protoplasts of Brassica napus", *Plant Cell Reports*, (Spring 1996); Kartha, K. et al., "In vitro Plant Formation from Stem Explants of Rape", *Physiol. Plant*, 31:217–220 (1974); Narasimhulu, S., et al., "Species Specific Shoot Regeneration Response of Cotyledonary Explants of Brassicas", *Plant Cell Reports*, (Spring 1988); Swanson, E., "Microspore Culture in Brassica", *Methods in Molecular Biology*, Vol. 6, Chapter 17, p. 159 (1990).

This invention also is directed to methods for producing a canola plant by crossing a first parent canola plant with a second parent canola plant wherein the first or second parent canola plant is an inbred canola plant of the new 44A53 cultivar. Further, both first and second parent canola plants can come from the new 44A53 cultivar. Thus, any such methods using the new 44A53 cultivar as a parent are within the scope of the present invention. Advantageously, the canola cultivar of the present invention can be used in crosses with other, different, *Brassica napus* canola inbreds to produce first generation ($F_1$) canola hybrid seeds and plants with superior characteristics.

As used herein, the term "plant" includes plant cells, plant protoplasts, plant cell tissue cultures from which canola plants can be regenerated, such as plant calli, plant clumps, and plant cells that are intact in plants or parts of plants, including embryos, pollen, ovules, flowers, pods, leaves, roots, root tips, anthers, stalks, and the like.

Industrial Applicability

The seed of the 44A53 cultivar, the plant produced from such seed, the hybrid canola plant produced from the crossing of the 44A53 cultivar, the resulting hybrid seed, and various parts of the hybrid canola plant can be utilized in the production of an edible vegetable oil or other food products in accordance with known techniques. The remaining solid meal component derived from seeds can be used as a nutritious livestock feed.

Performance Examples of the 44A53 Cultivar

Performance data for the new 44A53 cultivar is presented hereafter. Table 3 compares the agronomic traits of 44A53 to the same reference varieties earlier compared for morphological traits, namely, Defender, Excel, Legacy and 45A51.

TABLE 3

| Trait | Years | LSD 0.05 | 44A53 | DEFENDER | EXCEL | LEGACY | 45A51 |
| --- | --- | --- | --- | --- | --- | --- | --- |
| flower data 50% | 2 | — | 48.40 | 49.33 | 49.49 | 49.23 | — |
| maturity (days from planting) | 2 | 1.1281 | 95.23 | 94.67 | 95.25 | 95.33 | 95.43 |
| plant height | 2 | 3.92 | 103.19 | 124.23 | 124.72 | 120.97 | — |
| seed weight (grams per 1000 seeds) | 2 | — | 3.44 | 3.63 | 3.34 | 3.53 | — |
| oil % | 2 | — | 48.38 | 47.03 | 47.29 | 47.25 | — |
| protein % | 2 | — | 47.38 | 48.44 | 48.37 | 48.21 | — |
| erucic % of total acids | 2 | — | 0.28 | 0.38 | 0.99 | 0.09 | — |
| glucosinolate (Umol/g) | 2 | — | 11.10 | 14.33 | 17.84 | 11.58 | — |
| chlorophyll content (ppm) | 2 | — | — | 27.28 | 33.72 | 30.40 | — |
| blackleg resistant | 2 | — | 1.35 | 1.74 | 1.44 | 1.89 | — |
| white rust | 2 | — | 1.00 | 1.00 | 1.00 | 1.00 | 1.00 |

As can be seen from the table, cultivar 44A53 demonstrates superior black leg resistance and significantly shorter plant height. As noted earlier, Cultivar 44A53 also has a substantial degree of glyphosate resistance. Cultivar 44A53 clearly demonstrates a unique combination of agronomic traits that will make it an important cultivar for its area of adaptation.

Applicant(s) have made a deposit of at least 2500 seeds of Canola Cultivar 44A53 with the American Type Culture Collection (ATCC), Manassas, Va. 20110-2209 USA, ATCC Deposit No. PTA-4336. The seeds deposited with the ATCC on May 13, 2002 were taken from the deposit maintained by Pioneer Hi-Bred International, Inc., 800 Capital Square, 400 Locust Street, Des Moines, Iowa 50309-2340, since prior to the filing date of this application. Access to this deposit will be available during the pendency of the application to the Commissioner of Patents and Trademarks and, persons determined by the Commissioner to be entitled thereto upon request. Upon allowance of any claims in the application, the Applicant(s) will make available to the public pursuant to 37 C.F.R. §1.808, sample(s) of the deposit of at least 2500 seeds of Canola Cultivar 44A53 with the American Type Culture Collection (ATCC). 10801 University Boulevard. Manassas, Va. 20110-2209. This deposit of seed of 44A53 cultivar will be maintained in the ATCC Depsitory, which is a public depository, for a period of 30 years, or 5 years after the most recent request, or for the enforceable life of the patent, whichever is longer, and will be replaced if it ever becomes nonviable during that period. Additionally. Applicant(s) have satisfied all the requirements of 37 C.F.R. §§1.801–1.809, including providing an indication of the viability of the sample upon deposit. Applicant(s) have no authority to waive any restrictions imposed by law on the transfer of biological material or its transportation in commerce. Applicant(s) do not waive any infringement of their rights granted under this patent or under the Plant Variety Protection Act (7 USC 2321 et seq.)

The foregoing invention has been described in detail by way of illustration and example for purposes of exemplification. However, it will be apparent that changes and modifications such as single gene modifications and mutations, somaclonal variants, variant individuals selected from populations of the plants of the instant cultivar, and the like, likewise are considered to be within the scope of the present invention.

What is claimed is:

1. A canola seed designated 44A53, representative seed of said canola variety 44A53 having been deposited under ATCC Accession No. PTA-4336.

2. A canola plant, or parts thereof, produced by growing the seed of claim 1.

3. The canola plant part of claim 2 wherein said part is pollen.

4. The canola plant part of claim 2 wherein said part is an ovule.

5. A tissue culture of protoplasts or regenerable cells from the plant of claim 2.

6. A tissue culture according to claim 5, the cells or protoplasts of the tissue culture being of a tissue selected from the group consisting of: leaf, pollen, cotyledon, hypocotyl, embryos, root, pod, flower, shoot and stalk.

7. A canola plant regenerated from the tissue culture of claim 5, capable of expressing all the morphological and physiological characteristics of canola variety 44A53, representative seed of said canola variety 44A53 having been deposited under ATCC Accession No. PTA-4336.

8. A method for producing a first generation hybrid canola seed comprising: crossing the plant of claim 2 with a different inbred parent canola plant, and harvesting the resultant first generation hybrid canola seed.

9. The method of claim 8 for producing a first generation hybrid canola seed wherein the female parent is designated 44A53, representative seed of said canola variety 46A41 having been deposited under ATCC Accession number PTA-4336.

10. The method of claim 8 for producing a first generation hybrid canola seed wherein the male parent is designated 44A53, representative seed of said canola variety 46A41 having been deposited under ATCC Accession number PTA-4336.

11. A canola plant, or parts thereof, having all the physiological and morphological characteristics of the plant of claim 2.

12. The canola plant part of claim 11 wherein said part is pollen.

13. The canola plant part of claim 11 wherein said part is an ovule.

14. A tissue culture of protoplasts or regenerable cells from the plant of claim 11.

15. A tissue culture according to claim 14, the cells or protoplasts of the tissue culture being of a tissue selected from the group consisting of: leaf, pollen, cotyledon, hypocotyl, embryos, root, pod, flower, shoot and stalk.

16. A canola plant regenerated from the tissue culture of claim 14, capable of expressing all the morphological and physiological characteristics of canola variety 44A53, representative seed of said canola variety 44A53 having been deposited under ATCC Accession No. PTA-4336.

17. A method for producing a first generation hybrid canola seed comprising: crossing the plant of claim 11 with a different inbred parent canola plant, and harvesting the resultant first generation hybrid canola seed.

18. The method of claim 17 for producing a first generation hybrid canola seed wherein the different inbred canola plant is a male parent.

19. The method of claim 17 for producing a first generation hybrid canola seed wherein the different inbred canola plant is a female parent.

20. A method for producing a male sterile canola line comprising:

crossing the canola plant of claim 2 with a second canola plant to yield progeny canola seed, wherein the second canola plant has cytoplasmic male sterility and growing said progeny canola seed to yield an F1 male sterile canola plant.

* * * * *